(12) United States Patent
Cantrell

(10) Patent No.: US 6,433,235 B1
(45) Date of Patent: Aug. 13, 2002

(54) METHOD FOR CONVERTING METHANE-CONTAINING GASEOUS HYDROCARBON MIXTURES TO LIQUID HYDROCARBONS

(75) Inventor: Joel G. Cantrell, College Station, TX (US)

(73) Assignee: Bryan Research & Engineering, Inc., Bryan, TX (US)

( * ) Notice: Subject to any disclaimer, the term of this patent is extended or adjusted under 35 U.S.C. 154(b) by 0 days.

(21) Appl. No.: 09/591,367

(22) Filed: Jun. 9, 2000

(51) Int. Cl.[7] .............................. C07C 4/02; C07C 2/54; C10G 67/02; C10G 55/06
(52) U.S. Cl. .................. 585/331; 208/49; 208/58; 208/67; 208/69; 208/70
(58) Field of Search ................ 585/331; 208/44, 208/58, 67, 69, 70

(56) References Cited
U.S. PATENT DOCUMENTS

6,130,260 A  10/2000  Hall et al. ................. 518/703

*Primary Examiner*—Thuan D. Dang
(74) *Attorney, Agent, or Firm*—Browning Bushman P.C.

(57) ABSTRACT

An improved process for the conversion of normally gaseous methane-containing hydrocarbon mixtures, such as natural gas, to a normally liquid hydrocarbon product comprises separating the methane component of the gaseous mixture from the heavier hydrocarbon component, cracking the separated heavier hydrocarbon component at a relatively low temperature and optionally cracking the methane component at a relatively high temperature. The low temperature cracking product and any high temperature cracking product are separated into a light product of principally hydrogen and a heavy product comprising unsaturated hydrocarbons. This heavy product is reacted with methane in the presence of an acidic alkalization catalyst. The resulting product mixture is separated into a light product, a portion of which is recycled, and the normally liquid hydrocarbon product.

15 Claims, 5 Drawing Sheets

METHOD FOR CONVERTING METHANE-CONTAINING GASEOUS HYDROCARBON MIXTURES TO LIQUID HYDROCARBONS

FIELD OF THE INVENTION

This invention relates to an improved method of converting mixtures comprising major amounts of methane and minor amounts of normally gaseous higher hydrocarbons to normally liquid hydrocarbons. More particularly, the invention relates to an improved method of converting at least a substantial portion of methane-containing gaseous hydrocarbon mixtures to liquid hydrocarbons.

BACKGROUND OF THE INVENTION

Natural gas is typically a mixture of about 70 mole percent to about 98 mole percent of methane mixed with heavier hydrocarbons. These heavier hydrocarbons are mostly alkanes of two or more carbon atoms present in decreasing amounts according to increasing carbon number. Although these heavier hydrocarbons are typically present in small quantities relative to the methane and other normal gaseous materials such as carbon dioxide and even hydrogen sulfide are often present, as used herein, the term "natural gas" refers to a mixture which is predominantly methane with from about 2 mole percent to about 30 mole percent of other normally gaseous hydrocarbons, e.g., ethane, propane and butane. Removal of any other materials, such as carbon dioxide or water, if necessary, is accomplished by conventional methods.

Natural gas is an important energy source throughout much of the developed world including the United States. Particularly important is the use of nature gas as an energy source in its property of clean burning without the co-production of environmentally damaging oxides of nitrogen and sulfur. Unfortunately, the location of natural gas usage is often distant from the location of natural gas production so that transportation of the natural gas as by pipeline, or electrical energy produced therefrom, is often difficult and/or prohibitive because of the cost of such transportation.

It has long been desirable to convert natural gas to a liquid product which would facilitate transportation. Conventional methods for such conversion include liquefaction of the natural gas, partial oxidation of the natural gas to produce methanol and utilization of Fisher-Tropsch technology to convert methane to mixtures of carbon monoxide and hydrogen which are then converted to light olefins and paraffinic hydrocarbons. The process of U.S. Pat. No. 3,156,733 includes the pyrolysis of methane to produce acetylene and hydrogen followed by rapid quenching.

In copending U.S. patent application Ser. No. 09/199,502, filed Nov. 25, 1998, of Hall, et al., a thermal process is disclosed in which the natural gas is heated to a temperature where a portion of the methane component of the natural gas is cracked or pyrolyzed to produce hydrogen and reactive hydrocarbons such as ethylene and acetylene. This stream, also containing methane, is reacted in the presence of an acidic catalyst to produce a transportable liquid product which is predominantly pentane. Illustrative of the pentane production are the simplified equations which follow.

$$3\ CH_4 + C_2H_2 \rightarrow C_5H_{12} + H_2$$

$$3\ CH_4 + C_2H_4 \rightarrow C_5H_{12} + 2\ H_2$$

Unfortunately, the elevated temperatures required to crack the methane component is sufficiently high to destroy a portion of the higher hydrocarbons present in the natural gas as well as a portion of the reactive hydrocarbons produced by methane cracking through the formation of coke. This loss of potential liquid products of the overall process as by coke formation results in loss of economy of the process.

It would therefore be of advantage to provide an improved thermal process for the conversion of natural gas, but also of other methane-containing gaseous hydrocarbon mixtures, to normally liquid, more easily transportable, hydrocarbons in which the loss of hydrocarbons of two or more carbon atoms is minimized and the efficiency of the production of transportable liquid hydrocarbon is increased.

SUMMARY OF THE INVENTION

The present invention provides an improved method for the conversion of methane-containing gaseous hydrocarbon mixtures into normally liquid hydrocarbons of increased ease of transportation. The process includes the separation of the methane component of the methane-containing gaseous hydrocarbon mixture from the heavier hydrocarbon component. In the process of the invention, this heavier hydrocarbon component is subjected to cracking at a relatively low cracking temperature sufficient to crack the heavier hydrocarbons, but not crack an appreciable quantity of methane. This low temperature cracking process minimizes the loss of heavier hydrocarbons as by coking with a resulting overall efficiency of liquid product formation.

The methane-containing gaseous hydrocarbon mixtures to which the invention relates include natural gas but also light gases that are produced in petroleum refinery operations such as catalytic cracking and delayed coking. Gaseous hydrocarbon mixtures resulting from these operations are typically separated to recover the heavier, more valuable components with the light ends being used for fuel. Such streams often contain a significant portion of ethane, propane, alkanes and alkynes and hydrogen in addition to methane. The process of the invention is useful to convert these "waste gas" streams to more valuable liquid products.

The methane-containing gaseous hydrocarbon mixtures to which the process of the invention applies are those normally gaseous hydrocarbon mixtures containing at least about 40 mole percent methane and preferably at least about 55 mole percent methane with the remainder comprising saturated and unsaturated hydrocarbons as well as hydrogen. Of primary interest, as the methane-containing gaseous hydrocarbon mixture is natural gas. Natural gas, as obtained from the ground, often contains non-hydrocarbon materials such as water, hydrogen sulfide and carbon dioxide. As used herein, however, "natural gas" is used to describe a mixture of about 70 mole percent to about 98 mole percent of methane with the remainder being heavier hydrocarbons, mostly alkanes, of two or more carbon atoms present in decreasing amounts according to increasing carbon number.

In certain embodiments of the process of the invention, at least a major proportion of the separated methane is separately cracked in the substantial absence of the heavier hydrocarbon component of the natural gas feed. Remaining portions of the separated methane are reacted with unsaturated hydrocarbons in the presence of an acid catalyst to produce the normally liquid hydrocarbon product as illustrated by the above equations.

In another embodiment of the process of the present invention, the separated methane is not cracked but is in part used for the acid-catalyzed reaction of methane with cracked heavier hydrocarbons with any methane not so employed being removed from the process system and sent to disposal or used in the production of thermal or electrical energy as by conventional methods. Such energy is useful in portions of the overall process of the invention or in other applications.

In a specific embodiment of the invention, a novel method of separating the methane portion of the natural gas feed from the heavier hydrocarbon component is employed.

BRIEF DESCRIPTION OF THE DRAWINGS

FIG. 1 illustrates one embodiment of the process described and claimed in copending U.S. patent application Ser. No.09/199,502, filed Nov. 25, 1998. This figure is for illustration and comparison purposes only and does not represent the present invention. A natural gas stream is cracked at a relatively high temperature. The effluent from the cracking zone is pressurized and separated into a hydrogen product and a hydrocarbon product. The hydrocarbon product is mixed with inlet gas and reacted in the presence of an acidic catalyst. The resulting product is separated into an overhead product of hydrogen and light hydrocarbons, e.g., $C_1$–$C_4$, which is recycled. The bottoms product of this latter separation is the desired normally liquid hydrocarbon product, typically ranging from $C_4$ to $C_{12}$ and higher.

FIG. 2 illustrates one embodiment of the present invention. In this embodiment, the major portion of the methane-containing gaseous hydrocarbon feed is initially separated into a predominantly methane stream and a heavier hydrocarbon stream. These streams are separately cracked under differing cracking conditions. The resulting cracked streams are combined, pressurized, and separated into a hydrogen product stream and a hydrocarbon stream. The hydrocarbon stream is mixed with a portion of the gaseous feed and contacted in the presence of an acid catalyst. The resulting product stream is separated into a light fraction comprising hydrogen and light hydrocarbons, e.g., $C_1$–$C_4$, which is recycled. The heavier fraction comprises the desired normally liquid product.

In a somewhat different embodiment modification of the invention illustrated by FIG. 4, a methane-containing gaseous hydrocarbon feed is separated into a predominantly methane portion and a predominantly heavier hydrocarbon portion. The higher hydrocarbon portion is cracked at a relatively low cracking temperature, pressurized and separated into a hydrogen product and a hydrocarbon product. The hydrocarbon product is combined with the methane separated from the natural gas feed and the mixture is reacted in the presence of an acidic catalyst. The resulting reaction product is separated into a lighter stream of predominantly hydrogen and methane, a portion of which is vented with the remainder being recycled. The heavier portion of the reaction product is the desired normally liquid product.

A specific embodiment of the invention is illustrated by the novel separation procedure of FIG. 5. This procedure serves to separate the methane components of a methane-containing gaseous hydrocarbon feed from the heavier hydrocarbon component and is particularly, but not exclusively, employed in the processes of FIGS. 2 and 4. In this separation process, a methane-containing gaseous hydrocarbon feed is cooled by recycle streams and optionally by refrigeration before passing to a high pressure separator. The resulting high pressure separation produces an overhead vapor mixture of predominantly methane and a bottoms liquid stream of heavier hydrocarbons. The overhead vapor stream is depressurized to cool the stream and condense at least a portion of any heavier hydrocarbon present. This condensed hydrocarbon portion of the high pressure separator overhead is separated from methane present by means of a low pressure separator and then is combined with the liquid effluent of the high pressure separatorwhich has undergone depressurization. The cool liquid hydrocarbon stream and the cool gaseous methane stream are used to cool the incoming natural gas feed as by cross-exchange.

DESCRIPTION OF THE INVENTION

The present invention provides an improved process for the conversion of normally gaseous methane-containing hydrocarbons such as natural gas to normally liquid hydrocarbon product which is of particular value because of the ease of its transportation. The cracking of natural gas, in a pyrolysis unit or other conventional apparatus, followed by processing operations to increase the production of normally liquid product is known but has some inherent difficulties. The cracking of methane-containing gaseous hydrocarbons such as natural gas taken as a whole, requires the use of relatively high temperatures in order to crack the methane of the gaseous mixture. Under these relatively high-temperature conditions, a significant percentage of the higher hydrocarbon portion of the methane-containing gaseous hydrocarbons is effectively lost through formation of coke or other undesirable reactions. This loss of the heavier hydrocarbons results in the decrease of the desired normally liquid hydrocarbon product of the overall process. Yet, the presence of methane and the cracking products thereof, i.e., hydrogen and unsaturated hydrocarbons of two or more carbon atoms, are necessary in the overall process scheme. The hydrogen produced by methane cracking serves as a reaction diluent in various portions of the overall process with any hydrogen in excess of that required for diluent purposes being useful as a source of thermal or electrical energy in portions of this or other reaction schemes. The methane which is not cracked is also useful as a diluent or energy source and is also a reactant in the conversion of alkenes and alkynes resulting from cracking of methane as well as from cracking the heavier hydrocarbon portion of the gaseous feed.

Accordingly, there is a need for methane and higher hydrocarbon reactants. However, when mixtures of methane and higher hydrocarbons are cracked at the elevated temperatures of methane cracking, potential liquid product is lost through formation of coke or through other undesirable reactions. It has now been found to be useful to separate the methane component of the methane-containing gaseous hydrocarbon feed from the heavier hydrocarbon component and to crack the higher hydrocarbon component under conditions of temperature and pressure sufficient to cause cracking of the higher hydrocarbons but insufficient to cause substantial coke formation. The methane component, in some embodiments of the invention is separately cracked at relatively high temperatures. In such embodiments, the products of the two crackers are combined for further processing. In a different embodiment of this process of the invention, the methane component of the natural gas feed is not separately cracked but is in part used as a reactant in a subsequent portion of the overall process with an excess methane being available for energy production or other purposes. In the embodiment wherein the methane is cracked, the conditions of the cracking zone include a temperature above about 1450° K, preferably from about 1500° K to about 1900° K and a pressure from about 0.5 bar to about 10 bars, preferably from about 1 bar to about 3 bars. The residence time in the cracking zone is from about 1 millisecond to about 100 milliseconds. In contrast, where the heavier hydrocarbon portion of the methane-containing gaseous hydrocarbon feed is cracked in the substantial absence of methane, the cracking zone operates at a temperature from about 900° K to about 1400°K, preferably from about 1100° K to about 1250°, and a pressure from about 0.5 bar to about 10 bars, preferably from about 1 bar to about 3 bars. The residence time within this low temperature cracking zone is from about 1 millisecond to about 500 milliseconds, preferably from about 10 milliseconds to about 100 milliseconds.

The effluent from the heavier hydrocarbon cracking zone, with or without being mixed with the effluent of a methane cracking zone is compressed by a compressor or other conventional method to facilitate removal of non-hydrocarbons such as hydrogen upon passage to a cracked gas separation zone wherein the hydrocarbons are separated into an overhead fraction comprising primarily hydrogen and a bottoms fraction comprising primarily methane and unsaturated hydrocarbons, e.g. alkenes and alkynes. This separation is conducted by conventional methods such as cryogenic distillation, pressure swing adsorption, or a selectively permeable membrane. The operating conditions of the separation zone are dictated by the chosen technique. The overhead product is principally hydrogen and is recycled to a cracking zone or is removed from the system for disposal or energy use. The heavier or bottoms product from the cracked gas separation zone is mixed with a portion of the methane-containing gaseous hydrocarbon feed or methane obtained by separation of the components of that feed.

This mixture is passed to an alkylation zone where the mixture is contacted with an acid alkylation catalyst. Such catalysts are conventional and well-known and include hydrofluoric acid and sulfuric acid. Preferred acid catalysts are acidic zeolite catalysts, also conventional, and particularly preferred is the acidic zeolite catalyst H-ZSM-5. The alkylation zone is operated at a reaction temperature of from about 300° K to about 800° K, preferably from about 500° K to about 700° K, and a pressure from about 2 bars to about 30 bars, preferably from about 5 bars to about 15 bars.

Subsequent to reaction in the alkylation zone, the liquid product is separated in a conventional liquid product separation zone by conventional methods such as distillation or membrane separation. The heavier or bottoms product is the desired normally liquid product comprising saturated or aromatic hydrocarbons of 4 or more carbon atoms, most frequently from 4 to 12 carbon atoms inclusive. The lighter product of the liquid product zone comprises hydrogen, methane and small portions of $C_2-C_4$ hydrocarbons. Depending upon the particular embodiment of the invention, the light product is principally recycled to the cracked products separation zone with lesser portions being recycled to a methane high-temperature cracking zone or removed from the system for disposal or energy use.

DETAILED DESCRIPTION OF THE DRAWINGS

Figure 1:
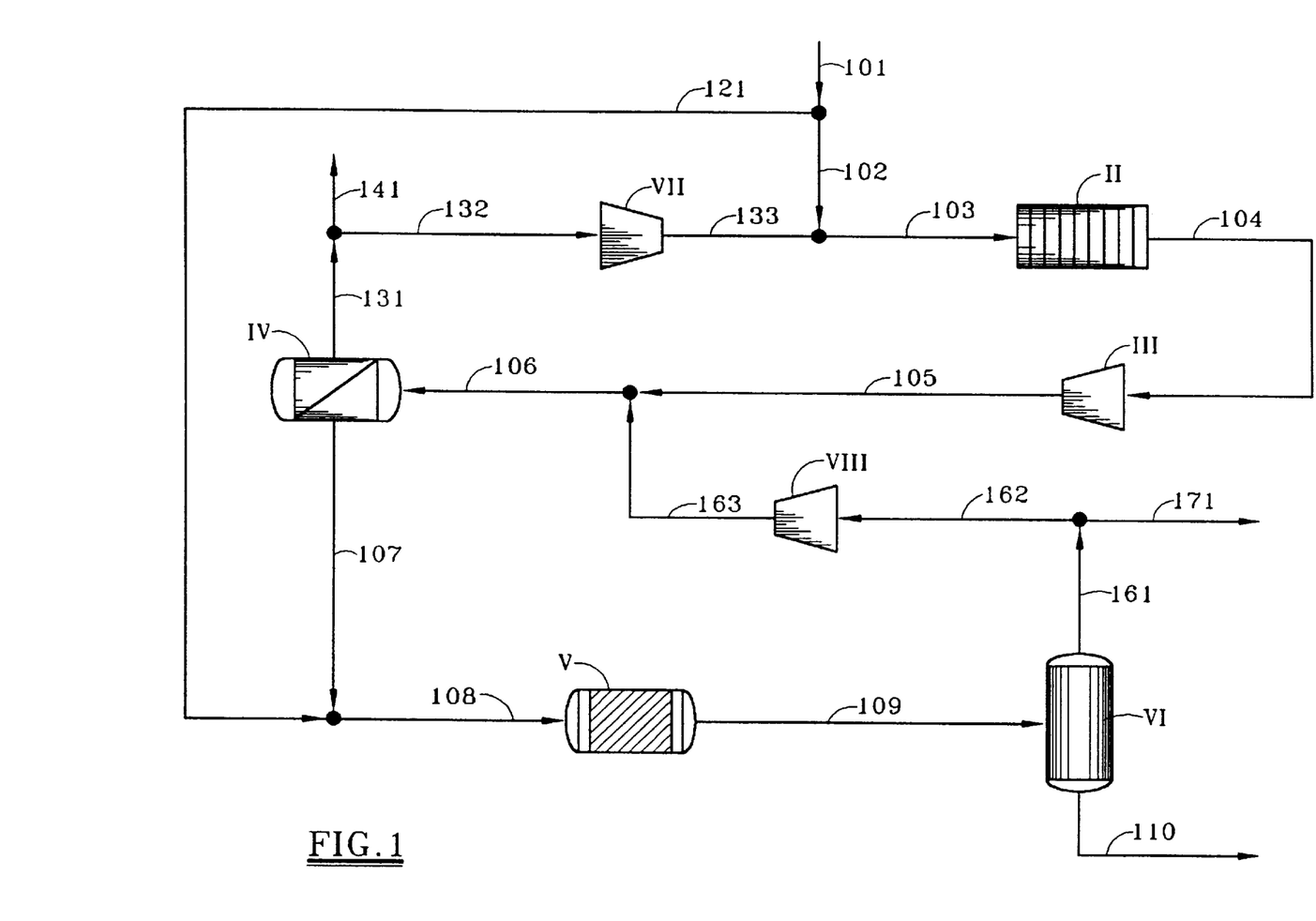

In FIG. 1, the process depicted is shown for comparison purposes and is not of the invention. In this process, natural gas is introduced via line 101, with a minor portion being sent by line 121 to serve as make-up for the alkylation reactor described below. The major portion of the natural gas feed passes by line 102 to where it is combined with recycled hydrogen from line 133 and then by line 103 to the cracking zone 11. In this cracking zone, operated at a temperature from 1600° K to 2500° K and a pressure of from 1 bar to 50 bars, a portion of the methane and substantially all of the heavier hydrocarbon component of the natural gas are cracked to produce a product mixture of hydrogen, methane and a mixture of unsaturated hydrocarbons such as alkenes, alkynes and aromatic compounds. Also produced from the heavier hydrocarbon component is coke.

The product of cracking zone 11 is passed by line 104 to a compression zone III, typically a compressor, which, if necessary, increases the pressure of the product stream. If the cracking zone product is at a suitable pressure, the compression step can be omitted. The product stream is then passed by line 105 to mix with a recycle stream of hydrogen and hydrocarbons in the $C_1-C_4$ range shown as line 163. The combined streams 105 and 163, now stream 106, are passed to a separation zone IV shown as a membrane system but which also could use other methods such as refrigeration, distillation, or pressure swing adsorption. The hydrogen overhead from the separation zone IV passes by line 131 to where it is split with a portion, line 141, going to disposal or use as an energy source and the remainder going by line 132 to a compression zone VII, typically a compressor, where the pressure is increased to approximately that of the inlet gas feed with which it is mixed. The mixture returns to the cracking zone 11 by lines 133 and 103.

The bottom product of the separation zone IV is a mixture of methane, hydrogen, recycled alkanes, and unsaturated hydrocarbons of two or more carbon atoms. This product leaves the zone by line 107, is combined with the minor portion of the natural gas feed, line 121, and the mixture passes by line 108 to a alkylation zone V where the methane present reacts with the unsaturated hydrocarbons in the presence of an acidic alkylation catalyst to produce a mixture of hydrogen and a range of hydrocarbon products of up to about 20 carbon atoms. This mixture passes by line 109 to a separation zone VI where it is separated into an overhead product of hydrogen and $C_1-C_4$ hydrocarbons exiting by line 161. A portion of this overhead is removed by line 171 for disposal or energy use. The major portion of the overhead product of separation zone VI passes by line 162 to a compression zone VIII, typically a compressor, where the pressure is raised to one compatible with separation zone IV. The light gas leaves the compressor by line 10 163 to where it is combined with gas from the cracking zone II and the mixture is sent by line 106 to separation zone IV.

The bottom product of separation zone VI, line 110, is the desired normally liquid product comprising a range of hydrocarbons from $C_4$ to $C_{12}$ and higher.

Figure 2:
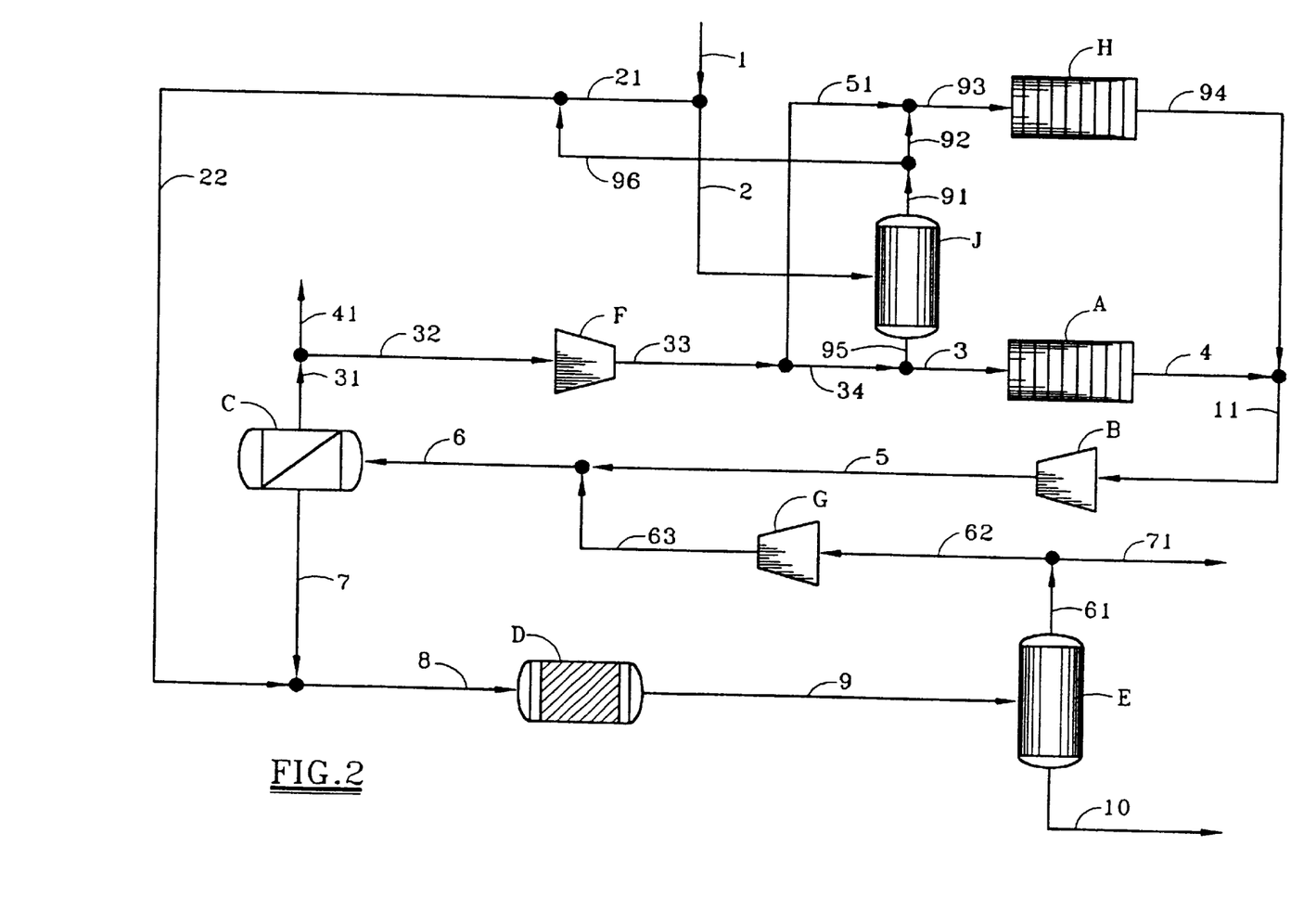

In the embodiment of the invention shown as FIG. 2, methane-containing gaseous hydrocarbon feed is introduced by line 1 where a split sends a minor portion by line 21 for use in an alkylation zone D. The remainder of the inlet gaseous hydrocarbon feed is sent by line 2 to an inlet gas separation zone J where the methane is substantially separated from the higher hydrocarbon portion of the feed. This separator can be a conventional unit such as a cryogenic demethanizer, but also is suitably a unit such as that illustrated by FIG. 5. The overhead of the inlet gas separation zone J, exits by line 91, where it is split, a portion of which, line 96, is mixed with some of the inlet gas, line 21, and fed to the alkylation zone D by lines 22 and 8. The remainder of the light gas from the inlet separation zone J, line 92, combines with a recycle stream, line 51, and then passes by line 93 to a relatively high temperature cracking zone H where. the methane is cracked to produce hydrogen and some unsaturated hydrocarbons. The bottom product of inlet gas separation zone J exits by line 95 and is mixed with the. recycle gas of line 34. The combined streams are passed by line 3 to a relatively low temperature cracking zone A where the heavier hydrocarbon component of the gaseous hydrocarbon feed is cracked at the relatively low cracking temperature with relatively little coke formation. The effluent from the low temperature cracking zone exits by line 4 to where it is combined with the effluent of the high temperature cracking zone H, line 94, and the mixture passes by line 11 to a compression zone B, typically a compressor. The compressed mixture, line 5, is mixed with recycled gas, line 63, and the mixture is sent through line 6 to cracked products separation zone C. This separation zone is conventional and is suitably a membrane system, a cryogenic distillation unit or a pressure swing adsorption system. The overhead from the separation zone C, primarily hydrogen with some methane, exits by line 31. This mixture is split with a portion removed through line 41 for disposal or energy use. The remainder of the separation zone C overhead passes by line 32 to a compression zone F, typically a compressor, where the pressure is raised to approximately that of the inlet gas. The exiting mixture, passes by line 33 to where it is split, with one portion being sent by line 51, mixed with inlet gas separation zone J overhead, line 92, and then going by line 93 to the relatively high temperature cracking zone H. The remainder of stream 33 passes by line 34 to where it is mixed with the bottom product of inlet gas separation zone J, introduced by line 95, and the mixture is sent to the relatively low temperature cracking zone A by line 3.

The bottom product of separation zone C exits by line 7, is mixed with a portion of the gaseous hydrocarbon feed and a portion of the light product of inlet separation zone J, line 22, and the resulting mixture passes by line 8 to the cracked products alkylation zone D wherein the mixture is contacted with an acidic alkylation catalyst at a temperature of from about 300° K to about 800° K, preferably from about 500° K to about 700° K, and a pressure of from about 2 bars to about 30 bars, preferably from about 5 bars to about 15 bars. The resulting product mixture of hydrogen, methane and saturated, unsaturated, and aromatic hydrocarbons by line 9, enters alkylation zone product separator E which serves to produce an overhead stream 61 comprising hydrogen and $C_1$–$C_4$ hydrocarbons and a liquid bottom product exiting by line 10. This bottom product is the desired liquid product containing saturated and aromatic hydrocarbons of 4 or more carbon atoms, most typically from 4 to 12 carbon atoms inclusive. The overhead product of the alkylatoin zone separator E exits by line 61 to where it is split, with a portion passing by line 71 to disposal or energy use and the remainder, line 62, is compressed at compression zone G, typically a compressor, to a pressure approximating that of cracked gas separation zone C. The compressed product, line 63, is mixed with combined cracking zone effluent, line 5, and the mixture is transferred to the cracked gas separation zone C by line 6.

Figure 3:
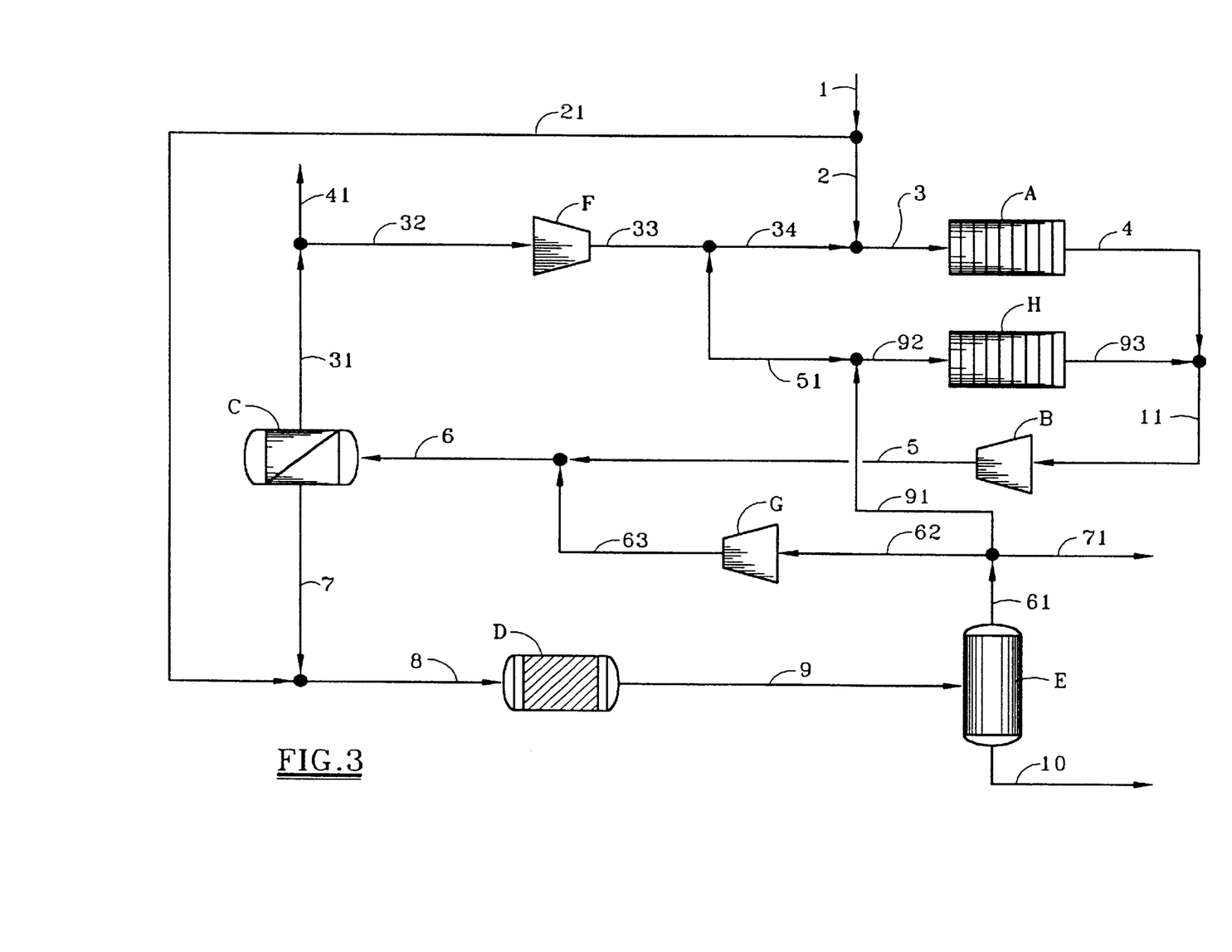
FIG. 3 depicts an alternate embodiment of the invention wherein a major portion of the methane-containing gaseous hydrocarbon feed is cracked in a cracking zone at relatively low temperatures. In this zone, the $C_2$ and heavier hydrocarbon portion of the feed is cracked. At the cracking temperatures employed, the methane portion of the gaseous feed is not reactive and by passing through the low-temperature cracking zone essentially unchanged is separated from the heavier hydrocarbon component of the it gaseous feed as well as the cracking products thereof. Methane recycled from a downstream portion of the process is cracked at a relatively high temperature in the substantial absence of higher hydrocarbon. The two cracking product streams are combined, pressurized and then separated into a hydrogen overhead product and a hydrocarbon bottoms product. This latter product is mixed with a portion of the gaseous feed and reacted in the presence of an acid catalyst. The product from reaction is separated into a light fraction of primarily hydrogen and methane which is in part recycled to the high-temperature cracking process described above. The heavier product of the reaction is the desired normally liquid product.

An alternate embodiment of the process of the invention is illustrated by FIG. 3 wherein the methane component of the gaseous hydrocarbon feed is separated from the heavier hydrocarbon component by selectively cracking the heavier hydrocarbon component in a relatively low temperature cracking zone wherein the methane passes through essentially unchanged. The methane is subsequently cracked in a relatively high temperature cracking zone.

In FIG. 3, methane-containing gaseous hydrocarbon feed enters the process by line 1 and is split. A portion of the inlet gas feed passes by line 21 for subsequent use in the alkylation zone D as discussed below. The major portion of the gaseous hydrocarbon feed is combined with recycle gas stream 34 and the mixture passes to a relatively low temperature cracking zone A operated at a temperature of from about 900° K to about 1400° K and a pressure of from about 0.5 bar to about 10 bars. The effluent from the low temperature cracking zone passes by line 4 and is mixed with effluent from a relatively high temperature cracking zone H, line 93, which operates after one cycle of the overall process has taken place. This mixture, line 11, is introduced to compression zone B, typically a compressor, where the pressure is elevated to that approximately equal to the pressure of cracked gas separation zone C. The compressed gas of stream 5 is mixed with a recycle gas, line 63, described below and the mixture enters cracked gas separation zone C by way of line 6. The overhead of cracked gas separator C, principally hydrogen and methane as stream 31, is split with a portion going to disposal or energy use, line 41, and the remainder, line 32, going to compression zone F, typically a compressor, where the pressure of the mixture is raised to a pressure approximately equivalent to that of the cracking zones. The pressurized mixture, line 33, is split with a first portion going by lines 34 and 3 to the low temperature cracking zone and a second portion going by lines 51 and 92 to the high temperature cracking zone. The bottoms product of cracked gas separation zone C exits by line 7 and is combined with the portion of inlet gas feed, line 21. The combined gas stream is sent by line 8 to cracked products alkylation zone D wherein the unsaturated hydrocarbons from the cracked gas separation zone C react with methane in the presence of an acidic alkylation catalyst. The effluent from alkylation zone D passes by line 9 to alkylation zone product separator E which produces an overhead product comprising hydrogen, methane and $C_1$–$C_4$ hydrocarbons and a bottoms product of a hydrocarbon mixture. This bottoms product, exiting by line 10, is the desired normally liquid hydrocarbon product of saturated, unsaturated, and aromatic hydrocarbons of 4 or more carbon atoms, most typically from 4 to 12 carbon atoms inclusive. The overhead product of alkylation zone product separator E exits by line 61 to where it is split into three portions. A first portion, stream 91, is combined with the recycle gas of line 51 and is sent to high temperature cracking zone H. A second portion, line 62, is compressed in compression zone G, typically a compressor, to a pressure approximating that of cracked gas separation zone C. The compressed portion, line 63, is mixed with mixed cracking zone effluent lines and sent by line 6 to the cracked gas separation zone C. The remaining portion of overhead is removed by line 71 for disposal or energy use.

Figure 4:
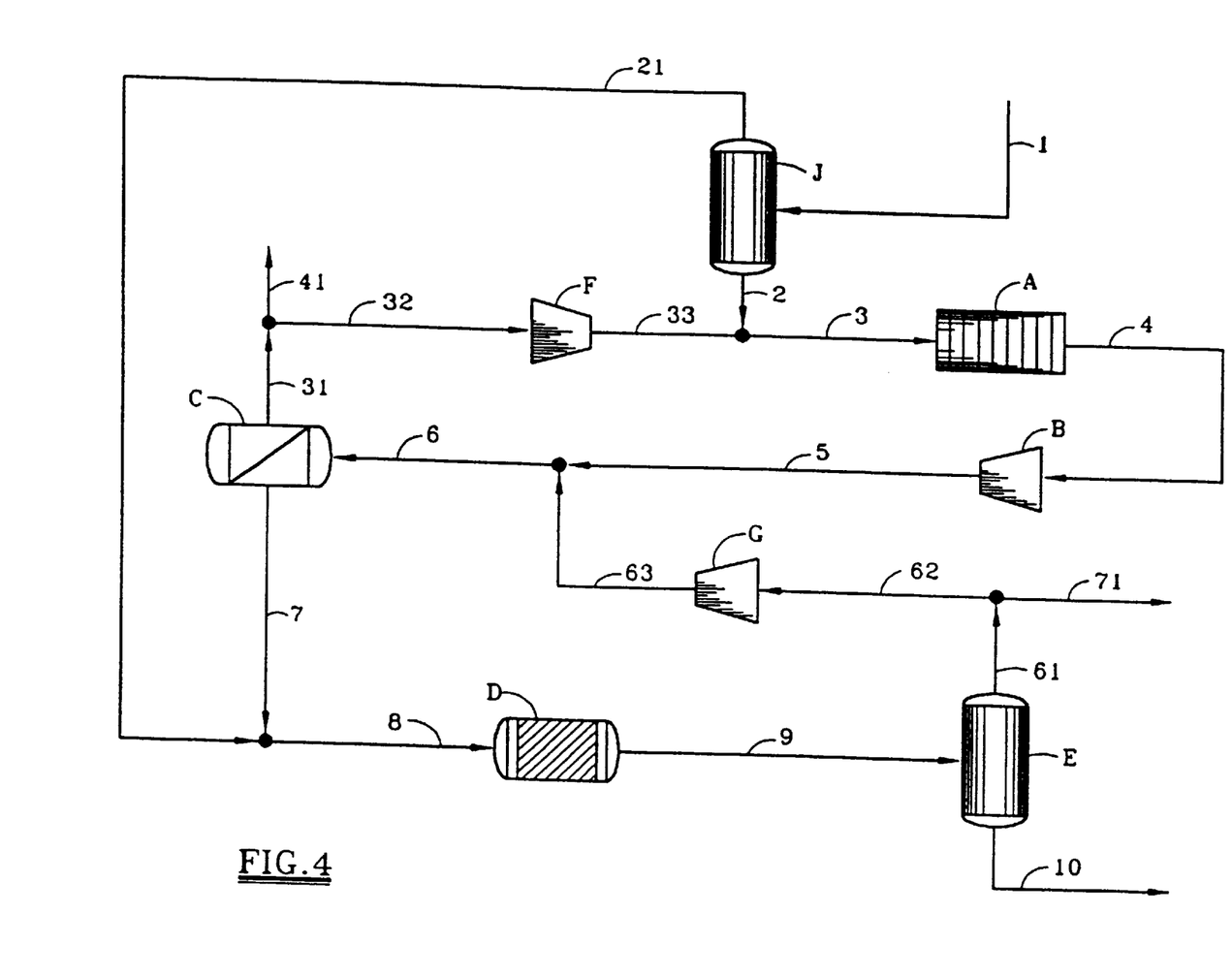

FIG. 4 represents a somewhat different embodiment of the invention. In this embodiment, the methane component of the methane-containing gaseous hydrocarbon feed is separated from the heavier hydrocarbon component. This heavier hydrocarbon component is cracked in a relatively low temperature cracking zone as in other embodiments but the methane component is not cracked. Instead, a portion of the methane is employed to react in the alkylation zone D with unsaturated hydrocarbons from cracked gas separation zone C. The remainder of the methane is utilized as a source of thermal or electrical energy in this or other processes.

Figure 5:
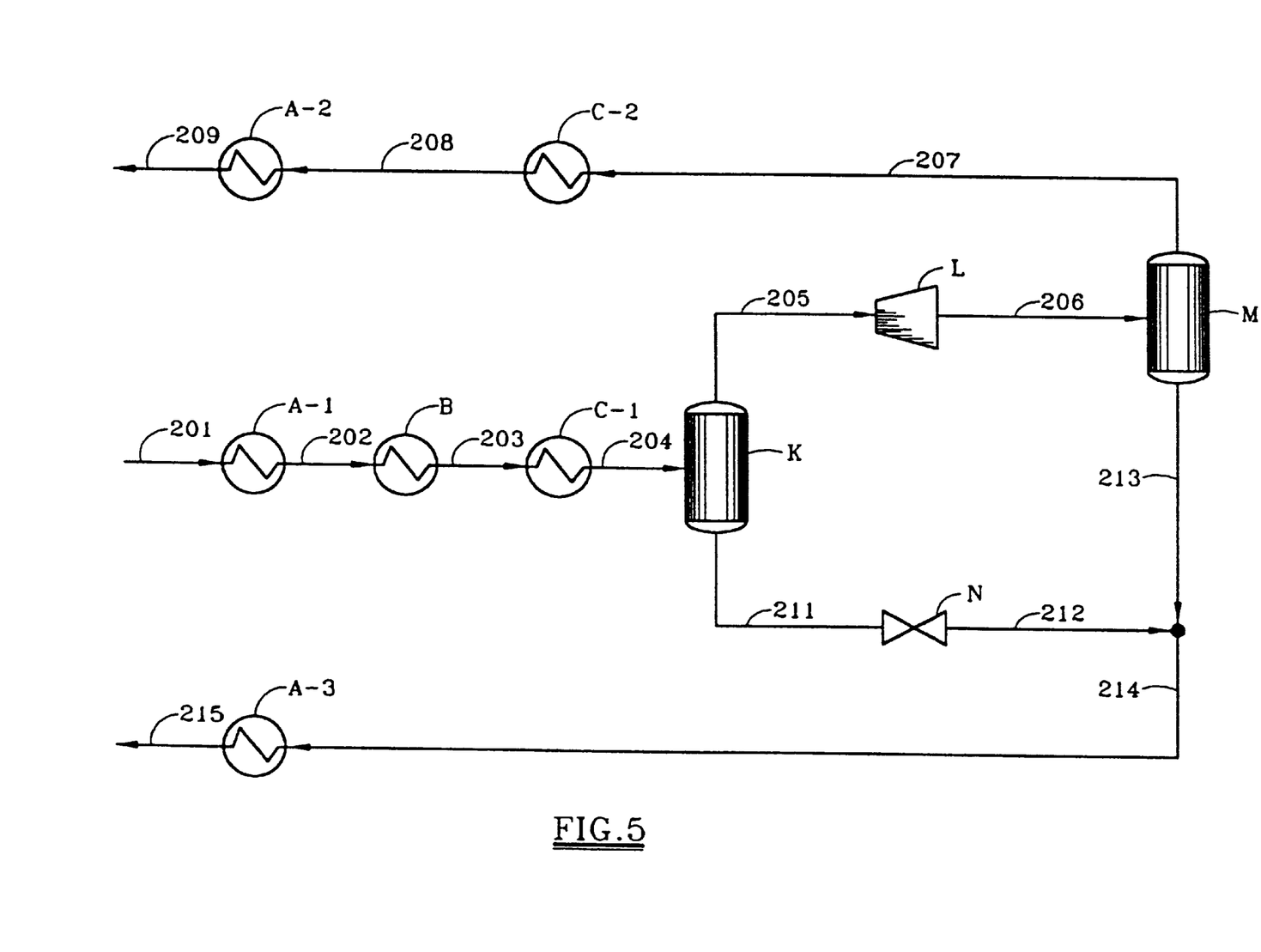

In FIG. 4, a methane-containing gaseous hydrocarbon feed is separated in inlet gas separation zone J by conventional means or by the novel procedure of FIG. 5. The overhead of the inlet gas separation zone is primarily methane which is transferred by line 21 for subsequent reaction with unsaturated hydrocarbons of cracked gas separation zone C in the cracked products alkylation zone D. The heavier product from inlet gas separation zone J comprises the heavier hydrocarbon portion of its gaseous feed. This product exits the separation zone by line 2, is combined with recycle gas from stream 33 and passes by line 3 to a low temperature cracking zone A wherein the heavier hydrocarbon component is converted largely to alkenes and alkynes. The unsaturated hydrocarbon mixture exits, line 4, and is elevated in pressure by compression zone B, typically a compressor, to a pressure approximating that of cracked gas separation zone C. The compressed gas is sent by line 5 to where it combines with recycle gas, line 63, and is transferred via line 6 to cracked products separation zone C. The overhead product of this separation zone, line 31, is largely hydrogen with a lesser amount of methane. A portion of this overhead product is removed by line 41 for disposal or energy use and the remainder, stream 32, is increased in pressure by compression zone F, typically a compressor, to that approximating the pressure of the low temperature cracking zone and then is transferred by lines 33 and 3 to the low temperature cracking zone A. The bottoms product of cracked products separation zone C, exiting by line 7, comprises a mixture of unsaturated hydrocarbons. This mixture is mixed with gaseous feed, stream 21, and is transported by line 8 to alkylation zone D wherein the unsaturated hydrocarbons react with methane in the presence of an acidic catalyst. The resulting product mixture is sent to alkylation product separation zone E by line 9. The light overhead of alkylation product separation zone E exits by line 61. This overhead, largely methane and hydrogen with minor amounts of $C_2$–$C_4$ hydrocarbon, is then split. One portion is removed as a stream 71 for disposal or energy use. The other portion, stream 62, is pressurized at compression zone G. typically a compressor, to a pressure approximately that of cracked gas separation zone C and passes by line 63 to where it is mixed with effluent from low temperature cracking zone A and returned by line 6 to separation zone C.

The bottoms product of alkylation product separation zone E, exiting by line 10, is the desired normally liquid hydrocarbon mixture of saturated and aromatic hydrocarbons of 4 or more carbon atoms, more typically 4 to 12 carbon atoms inclusive.

FIG. 5 represents a novel and preferred method of separating the methane component of a methane-containing gaseous hydrocarbon mixture inlet feed from the heavier hydrocarbon component. One application of this separation system comprises its use as an inlet feed separator in the process of FIGS. 2 and 4. However, the use of the separation system of FIG. 5 is not limited to such processes and it is broadly applicable to other separations of methane from heavier hydrocarbons such as ethane.

The high pressure gaseous hydrocarbon feed, typically at a pressure of from about 20 bars to about 100 bars, passes by lines 201, 202, 203 and 204 in which it is cooled, as described below, into a high pressure separation zone K operated at a temperature of from about 200° K to about 270° K. Within zone K, the feed is separated into an overhead vapor stream 205 comprising predominantly methane, and a bottoms liquid stream 211 which comprises the large majority of the ethane and the other heavier hydrocarbons of the gaseous hydrocarbon feed. The vapor stream 205 is depressurized typically across a valve or turboexpander to a pressure of from about 5 bars to about 20 bars with the temperature being cooled from about 100° K to about 200° K due to the expansion of the vapor. The pressure drop causes additional hydrocarbons of two or more carbon atoms to condense as the mixture passes by line 206 to a low pressure separation zone M. A cold vapor, stream 207, is obtained as overhead from the high pressure separation zone and is routed to high pressure/low pressure cross-exchangers C-2 and A-2 to provide cooling and thereby reduce the temperature of the feed. The liquid bottoms product of high pressure separation zone K passes by line 211 to a depressurization zone N. typically an expansion valve, to reduce the pressure on the liquid. The reduced pressure fluid passes by line 212 to where it is mixed with the bottoms product of the low pressure separation zone M, line 213, and the resulting mixture is sent by line 214 to heat exchanger A-3 where it, together with the vapor of line 208 from cross-exchanger C-2 is used to reduce the temperature of the inlet gas feed. The heat exchangers at A-1 (together with A-2 and A-3) and at C-1 (taken with C-2) are often sufficient to effect the desired reduction of gaseous hydrocarbon inlet feed. If desired, however, additional temperature reduction is obtained by employing optional refrigeration at exchanger B. The outlet lines from the overall separation process, lines 209 and 215, comprise the methane component and the stream containing the heavier hydrocarbon component of the gaseous hydrocarbon inlet feed, respectively.

While preferred embodiments of the present invention have been illustrated in detail, it is apparent that modifications and adaptations of the preferred embodiments will occur to those skilled in the art. However, it is to be expressly understood that such modifications and adaptations are within the spirit and scope of the present invention as set forth in the following claims.

What is claimed is:

1. The process of converting a normally gaseous, methane-containing, hydrocarbon feed to a normally liquid hydrocarbon product which comprises:

a) separating the methane component of the feed from the heavier hydrocarbon component, b) cracking the higher hydrocarbon component resulting from the separation of the methane component and heavier hydrocarbon component of the feed at a relatively low temperature in a low temperature cracking zone, c) optionally cracking a portion of the methane component of the feed at a relatively high temperature in a high temperature cracking zone, d) passing the effluent from the low temperature cracking zone mixed with any effluent from the high temperature cracking zone to a cracked gas separation zone wherein is produced a light fraction comprising hydrogen and a heavier hydrocarbon fraction comprising unsaturated hydrocarbons, e) passing the heavier hydrocarbon fraction, mixed with methane to an alkylation zone wherein the heavier hydrocarbon product is reacted with the methane in the presence of an acidic alkylation catalyst, f) separating the resulting alkylation zone reaction products in a liquid zone product separator to produce a light product mixture and a heavier product of normally liquid hydrocarbon, and g) recycling a portion of the light product of the alkylation zone product separator to the cracked gas separation zone.

2. The process of claim 1, wherein the low temperature cracking zone is operated at a temperature of from about 900° K to about 400° K and a pressure from about 0.5 bar to about 10 bars.

3. The process of claim 2, wherein the high temperature cracking zone is operated at a temperature of from about 1450° K to about 1500° K and a pressure from about 0.5 bar to about 10 bars.

4. The process of claim 3 wherein the normally gaseous, containing hydrocarbon feed is natural gas.

5. The process of claim-wherein the alkylation zone operates at a temperature of from about 300° K to about 800° K and a pressure from about 2 bars to about 30 bars, and the acidic catalyst is an acidic zeolite catalyst.

6. The process of converting a normally gaseous, methane-containing, hydrocarbon feed to a normally liquid hydrocarbon product which comprises:

a) separating the methane component of a portion of the feed from the heavier hydrocarbon component of the feed, b) cracking the resulting separated higher hydrocarbon component at a relatively low temperature in a low temperature cracking zone, c) cracking the methane component at a relatively high temperature in a high temperature cracking zone, d) combining the effluent from the low temperature cracking zone and the effluent from the high temperature cracking zone, e) separating the resulting combined effluent in a cracking product separation zone into a light fraction comprising hydrogen and a heavier hydrocarbon fraction comprising unsaturated hydrocarbons, f) combining the heavier hydrocarbon fraction with the remaining portion of the feed and reacting the resulting mixture in the presence of an acidic alkylation catalyst in an alkylation zone, and g) separating the resulting alkylation zone product mixture into a light product, a portion of which is recycled to the cracked products separation zone and a heavy product comprising the normally liquid hydrocarbon product.

7. The process of claim 6, wherein the low temperature cracking zone is operated at a temperature of from about 900° K to about 400° K and a pressure from about 0.5 bars to about 10 bars, and the high temperature cracking zone is operated at a temperature from about 1450° K to about 1500° K and a pressure of from about 0.5 bar to about 10 bars.

8. The process of claim 7, wherein the methane-containing hydrocarbon feed is natural gas of from about 70 mole percent to about 98 mole percent methane.

9. The process of claim, 8, wherein the residence time in the low temperature cracking zone is from about 1 millisecond to about 500 milliseconds and the residence time in the high temperature cracking zone is from about 1 millisecond to about 100 milliseconds.

10. A process of converting a normally gaseous, methane-containing hydrocarbon feed to a normally liquid hydrocarbon product which comprises:

a) separating the methane component of a major portion of the normally gaseous, methane-containing hydrocarbon feed from the heavier hydrocarbon component of the gaseous feed while passing through a relatively low temperature cracking zone, the-methane component being substantially unchanged and the heavier hydrocarbon component being cracked to produce unsaturated hydrocarbon products, b) passing the resulting mixture of methane component and cracked heavier hydrocarbon component to a cracked product separation zone to separate a light fraction containing methane and hydrogen and a heavier hydrocarbon fraction containing unsaturated hydrocarbons, c) recycling a portion of the light fraction to the low temperature cracking zone and passing the remaining portion of the light fraction to a relatively high temperature cracking zone and combining the effluent from the high temperature cracking zone with effluent from the low temperature cracking zone during passage to the cracked products separation zone, d) combining the heavier hydrocarbon product of the cracked products separation zone with the minor portion of the normally gaseous, methane-containing hydrocarbon feed and reacting the resulting mixture in the presence of an acidic alkylation catalyst in an alkylation zone, and e) separating the resulting product mixture of the alkylation zone into a light product, a first portion of which is recycled to the cracked product separation zone and a second portion of which is recycled to the high temperature cracking zone, and a heavier product of normally liquid hydrocarbons.

11. The process of claim 10, wherein the low temperature cracking zone operates at a temperature of from about 900° K. to about 1400° K. and a pressure from about 0.5 bar to about 10 bars with a residence time of from about 1 millisecond to about 500 milliseconds.

12. The process of claim 11 wherein the hydrocarbon feed is natural gas of from about 70 mole percent to about 98 mole percent methane.

13. The process of converting a normally gaseous, methane-containing hydrocarbon feed into a normally liquid hydrocarbon which comprises:

a) separating the methane component of the feed from the heavier hydrocarbon component, b) cracking the heavier hydrocarbon component in a cracking zone operating at a relatively low temperature, c) passing the effluent of the low temperature cracking zone to a cracked product separation zone wherein there results a light fraction, a portion of which is recycled to the low temperature cracking zone, and a heavy faction comprising unsaturated hydrocarbons, d) mixing the heavy fraction with the methane component of the feed and reacting the resulting mixture in the presence of an acidic alkylation catalyst in an alkylation zone, and e) separating the resulting products of the alkylation zone into a light product, a portion of which is recycled to the cracked gas separation zone, and a heavier product of normally liquid hydrocarbons.

14. The process of claim 13, wherein the cracking zone operating at a relatively low temperature operates at a temperature of from about 900° K. to about 1400° K.

15. The process of claim 14, wherein the hydrocarbon feed is natural gas.

* * * * *

UNITED STATES PATENT AND TRADEMARK OFFICE
CERTIFICATE OF CORRECTION

PATENT NO.    : 6,433,235 B1
DATED         : August 13, 2002
INVENTOR(S)   : Joel G. Cantrell It is certified that error appears in the above-identified patent and that said Letters Patent is hereby corrected as shown below:

<u>Column 11,</u>
Lines 16 and 60, change "400º K" to -- 1400º K --
Line 24, add -- 4 -- after "claim" and delete the dash "-"

<u>Column 12,</u>
Line 13, delete the dash "-" between "the" and "methane"

Signed and Sealed this

Twenty-fifth Day of February, 2003

JAMES E. ROGAN
*Director of the United States Patent and Trademark Office*